United States Patent [19]

Ross et al.

[11] Patent Number: 5,102,926

[45] Date of Patent: * Apr. 7, 1992

[54] CITRATE ESTER COMPOUNDS AND PROCESSES FOR THEIR PREPARATION

[75] Inventors: Louis R. Ross, Newark; Paul R. Krumlauf, Thornville; Edward L. Wilson, Newark, all of Ohio

[73] Assignee: Owens-Corning Fiberglas Corporation, Toledo, Ohio

[*] Notice: The portion of the term of this patent subsequent to Feb. 18, 2009 has been disclaimed.

[21] Appl. No.: 517,863

[22] Filed: May 2, 1990

Related U.S. Application Data

[63] Continuation-in-part of Ser. No. 428,548, Oct. 30, 1990.

[51] Int. Cl.$^5$ .............................................. C08K 5/01
[52] U.S. Cl. .................................. 523/511; 523/507; 528/192; 560/198
[58] Field of Search .................. 523/507, 511; 528/192; 560/198

[56] References Cited

U.S. PATENT DOCUMENTS

| | | |
|---|---|---|
| 3,549,586 | 12/1970 | Smith et al. |
| 3,650,997 | 3/1972 | Weisfeld et al. |
| 3,652,502 | 3/1972 | Jackson, Jr. |
| 3,701,748 | 10/1972 | Kroekel |
| 3,772,241 | 11/1973 | Kroekel |
| 3,833,411 | 9/1974 | Vazirani ........................ 117/232 |
| 3,883,612 | 5/1975 | Pratt et al. .................... 260/862 |
| 3,931,422 | 1/1976 | Bateman et al. .............. 427/424 |
| 3,931,438 | 1/1976 | Beall et al. .................... 428/218 |
| 4,100,229 | 7/1978 | Schwartz, Jr. ................. 526/15 |
| 4,160,758 | 7/1979 | Gardner ........................ 525/168 |
| 4,263,199 | 4/1981 | Atkins ........................... 525/19 |
| 4,275,189 | 6/1981 | Danick et al. ................. 528/296 |
| 4,288,571 | 9/1981 | Comstock et al. ............. 525/170 |
| 4,293,686 | 10/1981 | Gardner ........................ 528/192 |
| 4,374,215 | 2/1983 | Atkins ........................... 523/514 |
| 4,387,211 | 6/1983 | Yasuda et al. ................. 528/179 |
| 4,446,301 | 5/1984 | Belote et al. .................. 528/295.3 |
| 4,459,401 | 7/1984 | Sekmakas et al. ............. 528/296 |
| 4,473,544 | 9/1984 | Ochsenbein et al. .......... 523/511 |
| 4,507,339 | 3/1985 | Carbo et al. ................... 428/35.8 |
| 4,525,498 | 6/1985 | Atkins et al. .................. 523/511 |
| 4,525,524 | 6/1985 | Tung et al. .................... 524/601 |
| 4,555,534 | 11/1985 | Atkins ........................... 523/507 |
| 4,622,354 | 11/1986 | Iseler et al. .................... 523/527 |
| 4,735,995 | 4/1988 | Chettiath ....................... 525/301.5 |
| 4,787,989 | 11/1988 | Fanelli et al. .................. 252/8.6 |
| 4,873,286 | 10/1989 | Gallucci et al. ............... 525/92 |

FOREIGN PATENT DOCUMENTS

| | | |
|---|---|---|
| 075765 | 4/1983 | European Pat. Off. |
| 335406 | 10/1989 | European Pat. Off. |

OTHER PUBLICATIONS

STN International Search Results Abstract relates to the European Application No. 335406.

Primary Examiner—Paul R. Michl
Assistant Examiner—Edward Cain
Attorney, Agent, or Firm—Patrick P. Pacella; Ted C. Gillespie; Catherine B. Martineau

[57] ABSTRACT

Citrate ester compositions which are useful as compatible components in a resinous system for sheet molding compositions and have a general formula

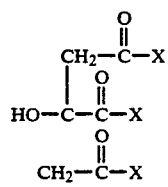

wherein X is selected from the group consisting of $-(OC_3H_6)_3-OCH_3$ and OH are disclosed. Also disclosed is a sheet molding composition which includes a four component resinous system comprising (a) an unsaturated polyester comprising a polycondensation product of one or more dihydric alcohols and one or more ethylenically unsaturated polycarboxylic acids; (b) one or more low-profile thermoplastic polymer additives which cause phase separation and internal voids during the curing reaction; (c) one or more olefinically unsaturated monomers which copolymerize with the unsaturated polyester; and, (d) one or more compatible components which remain compatible when the polyester and monomer cure and impart improved surface characteristics when added to typical low-profile resin systems.

16 Claims, No Drawings

CITRATE ESTER COMPOUNDS AND PROCESSES FOR THEIR PREPARATION

BACKGROUND OF THE INVENTION

The present invention is a continuation-in-part of Ser. No. 07/428,548 filed Oct. 30, 1989.

The present invention provides improved surface smoothness in unsaturated polyester resin compositions that contain low-profile additives. More specifically, these unsaturated resin compositions contain low-profile additives and compatible compounds. The present invention relates in particular to citrate ester compatible compounds and the processes for their preparation.

Unsaturated polyester resin compositions are finding increased use in the automotive industry as compositions from which component parts especially body panels can be molded. These compositions contain, in addition to the unsaturated polyesters, so-called "low-profile" additive components which are thermoplastic polymers that act to prevent undesirable shrinkage as the composition is being molded into a thermoset article. Low-profile additives are added to unsaturated polyester compositions for the purpose of obtaining a composition which can be molded into thermoset articles, where the surfaces of the molded articles truly reflect the surface characteristics of the mold.

Two types of low-profile systems are commonly used commercially, one-pack and two-pack. In one-pack systems, the polyester, styrene and low-profile additive components are mutually compatible, i.e., no gross separation occurs when a mixture is allowed to stand. In contrast, two-pack systems form distinct phases if the components are allowed to stand. These need to be mixed immediately prior to use. In either case phenonmena occur that allow these resins to microscopically compensate for shrinkage.

It is the ability of the low-profile resins to compensate for shrinkage that leads to the usefulness of these resins. This shrinkage compensation is largely a result of a micro-phase separation that occurs in these unsaturated polyester resin systems. The micro-phase separation occurs during the cure phase for both the one-pack and two-pack systems.

Prior to cure the low-profile additive is at least partly soluble in the polyester/styrene solution. As the polyester/styrene mixture crosslinks, the low-profile thermoplastic additive and copolymer become increasingly less compatible and a two-phase (domain-matrix) type morphology results. This micro-phase separation leads to the formation of a porous structure as the opposing internal stresses of thermal expansion and polymerization shrinkage occur. In many unsaturated polyester resin compositions the porous structure is a result of microfracturing of the curing resins which gives rise to void formation. Unsaturated polyester resins have been developed which have essentially zero shrinkage and which, in fact, expand upon curing.

In addition to unsaturated polyester resins, the sheet molding compound formulations typically contain other ingredients including, for example, chemical thickeners. In such systems, an alkaline material such as magnesium oxide or magnesium hydroxide is added to, for example, an uncured polyester along with fillers, glass fiber, and other standard materials. The alkaline material interacts with the residual acidity in the polyester and, usually, the low-profile additive to build viscosity. This process is referred to as maturation and usually takes several days. If two-pack resin systems are used, care has to be taken to avoid gross phase separation. After the maturation process is complete, the thickened systems are handlable and can easily be placed into compression molds either by hand or by machine.

Although the use of low-profile additives as described as three component mixtures do effect some degree of improvement in the anti-shrinkage characteristics of the unsaturated polyester compositions, it has been found that significant improvements could yet be made on surface smoothness and processing characteristics.

PRIOR ART

Low-profile resins have been described that contain unsaturated polyester resins, thermoplastic low-profile additives, and a polymerizable monomer, usually styrene. In addition to these components other materials have been added to low-profile systems to improve specific properties.

The Iseler, et al. U.S. Pat. No. 4,622,354 describes "phase stabilizing agents" that comprise a selected group of compounds from three classes; fatty acids, dimer acids and polyester polyols. When used in an SMC formulation where the thermoplastic low-profile additive is polymethylmethacrylate and a urethane prepolymer is included, the phase stablizing agent reduces the gross separation that occurs during the maturation process. The resin compositions described by Iseler et al. are two-pack systems that formerly phase-separated during maturation prior to the addition of the phase stabilizers.

The Ochsenbein et al. U.S. Pat. No. 4,473,544 describes an anti-shrink additive with a tri- or tetrafunctional polyether condensation product of propylene oxide on a triol or tetrol wherein the condensation product is acidified in such a manner that it possesses at least one terminal acidic functional group per elementary molecule. This material is used as a low-profile additive.

The Atkins U.S. Pat. No. 4,555,534 describes low-shrink pigmentable unsaturated polyester resins which comprises a polyester resin comprising the reaction product of an olefinically unsaturated dicarboxylic acid or anhydride and a polyol, an olefinically unsaturated monomer, a thickening agent, a pigment, a carboxylated vinyl acetate polymer low-profile additive, and a surface active compound. The Atkins '534 patent describes low-shrink resins having improved uniformity of pigmentation in internally pigmented thickened polyester-modling compositions. These pigmentable resin systems are low-shrink, and not low-profile. The surface quality of these pigmentable systems is considerably inferior to surfaces required for automotive appearance applications.

Although the use of low-profile additives and thickening agents, as described, do effect some degree of improvement in the antishrinkage and surface smoothness characteristics of the unsaturated polyester compositions, they are unable to achieve the degree of surface smoothness required of today's thermoset molded articles.

SUMMARY OF THE INVENTION

The present invention provides a means for improving the surface smoothness in low-profile resin compositions which are compression or injection molding into useful articles. In one aspect, the invention comprises an improved sheet molding composition that includes a four component resinous system comprising:

(a) an unsaturated polyester comprising a poly condensation product of one or more dihydric alcohols and one or more ethylenically unsaturated polycarboxylic acids;

(b) one or more low-profile additives comprising thermoplastic polymers which cause phase separation and internal voids during the curing reaction;

(c) one or more olefinically unsaturated monomers which copolymerize with the unsaturated polyester; and, (d) one or more components that remain compatible when the polyester and monomer cure and contain one or more polyoxyethane substituents.

In another aspect, the invention relates to novel compositions which are useful as compatible components in a resinous system for sheeting molding. The novel compounds are citrate ester compounds containing one or more polyoxyethane substituents having a general formula

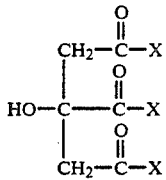

I wherein X is selected from the group consisting of $-\!\!\!-\!\!O-\!\!C_3H_6-\!\!\!)\!-\!\!OCH_3$ and OH.

The four component resinous system imparts improved surface smoothness when used with other known conventional ingredients for low-profile resin systems used in making sheet molding compositions.

DESCRIPTION OF INVENTION

The present invention relates to the discovery of the use in a group of components which remain compatible with a curing unsaturated polyester resin, and monomer used in a low-profile resin system. When these compatible components are included in combination with low-profile additives and used in sheet molding compositions, articles with very smooth surfaces may be molded. Additionally, the flow during the molding process is improved to the point that rapidly curing formulations may be composed, consequently the molding time is drastically reduced. Also, these compounds are helpful in controlling the thickening of SMC.

The unsaturated polyester components of the four component resinous system comprises the polycondensation reaction product of one or more dihydric alcohols and one or more ethylenically unsaturated polycarboxylic acids. By polycarboxylic acid is generally meant the polycarboxylic or dicarboxylic acids or anhydrides, polycarboxylic or dicarboxylic acid halides, and polycarboxylic or dicarboxylic esters. Suitable unsaturated polycarboxylic acids, and the corresponding anhydrides and acids halides that contain polymerizable carbon-to-carbon double bonds may include maleic anhydride, maleic acid, and fumaric acid. A minor proportion of the unsaturated acid, up to about forty mole percent, may be replaced by dicarboxylic or polycarboxylic acid that does not contain a polymerizable carbon-to-carbon bond. Examples of which include O-phthalic, isophthalic, terephthalic, succinic, adipic, sebacic, methyl-succinic, and the like. Dihydric alcohols that are useful in preparing the polyesters include 1,2-propane diol (hereinafter referred to as propylene glycol), dipropylene glycol, diethylene glycol, 1,3-butanediol, ethylene glycol, glycerol, and the like. Examples of suitable unsaturated polyesters are the polycondensation products of (1) propylene glycol and maleic and/or fumaric acids; (2) 1,3-butanediol and maleic and/or fumaric acids; (3) combinations of ethylene and propylene glycols (approximately 50 mole percent or less of ethylene glycol) and maleic and/or fumaric acid; (4) propylene glycol, maleic and/or fumaric acids and dicyclopentadiene reacted with water. In addition to the above described polyesters one may also use dicyclopentadiene modified unsaturated polyester resins as described in the Pratt et al. U.S. Pat. No. 3,883,612. These examples are intended to be illustrative of suitable polyesters and are not intended to be all-inclusive. The acid number to which the polymerizable unsaturated polyesters are condensed is not particularly critical with respect to the ability of the low-profile resin to be cured to the desired product. Polyesters which have been condensed to acid numbers of less than 100 are generally useful, but acid numbers less than 70 are preferred. The molecular weight of the polymerizable unsaturated polyester may vary over a considerable range, but ordinarily those polyesters useful in the practice of the present invention have a molecular weight ranging from 300 to 5000, and more preferably, from about 500 to 5000.

In preferred embodiments, the unsaturated polyester is present in amounts ranging from about 20 to 45 percent, by weight, based on the total four component resinous system comprising the unsaturated polyester, the low-profile additive, monomer and compatible component containing one or more polyxyethane substituents. Especially preferred concentrations of the unsaturated polyester are in the 28 to 35 percent, by weight, range.

Low-profile additives are materials that when mixed in an unsaturated polyester and cured, result in a multiphase system. If the low-profile additive and the unsaturated polyester are compatible (from the standpoint that a gross phase separation does not take place) before cure, the system is known as a one-pack. Those mixtures which tend to separate into two or more layers on standing are known as a two-pack resin systems. This does, however, necessitate mixing immediately before use. Some polymers that are useful as low-profile additives include homopolymers and copolymers of acrylic and methacrylic acid esters, cellulose acetate butyrate, vinyl acetate homopolymers and copolymers, polyurethanes prepared from polyisocyanates, preferably diisocyanates, and polyether polyols, numerous saturated polyesters, polycaprolactone, styrenebutadiene copolymers, some modified celluloses, and certain alkyl oxide polymers. The above list of low-profile additives is not intended to list all low-profile additives but rather to show examples of materials which ave been used to cause the multiphase morphology present in low profile resins. In preferred embodiments the thermoplastic additive is present in amounts ranging from 5 to 30 percent, by weight, based on the total four component resinous system. Especially preferred concentrations of thermoplastic additive are in the 7 to 20 percent, by weight range.

The monomer component comprises materials that copolymerize with the unsaturated polyester. The olefinically unsaturated monomer that is copolymerizible with the unsaturated polyester is most generally styrene, however, methyl-styrene is also useful. In preferred embodiments the monomer is present in amounts ranging from 25 to 65 percent, by weight, based on the total four component resinous system. Especially preferred concentrations of monomer are in the 35 to 50 percent, by weight range.

In the present invention one or more components are added which are compatible with the unsaturated polyester and monomer during cure. According to the present invention, these compatible components give the added benefits of surface smoothness and better flowability, when compared with low-profile resin compositions without the compatible components. In the preferred embodiments the compatible component is present in amounts ranging from 0.5 to 15 percent, by weight, based on the total four component resinous system. Especially preferred concentrations of the compatible components are in the 1 to 8 percent, by weight range.

The compatible components of the present invention contains one or more polyoxyethane substituents having a general structure:

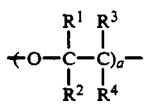

where $R^1$, $R^2$, $R^3$, and $R^4$, are selected from the group consisting of hydrogen, cycloalkyl, lower alkyl, phenyl, phenyl substituted by halogen, lower alkyl, acyl, or lower alkoxy; $R^1$, $R^2$, $R^3$ and $R^4$ may be the same or different; and a is an integer between about 1 and 200, and in some embodiments a is less than 100 and in certain embodiments a is between 3 and 70.

The following terms used herein: "lower alkyl", "lower alkoxy", lower phenyl", "cycloalkyl" and "acyl" generally contain from 1 to 50 carbons, as is well understood by those skilled in the art.

One example of compatible components that contain polyoxyethane substituents are polymers such as apolyalkylene oxide which has a molecular weight of betwen about 200–5000. The molecular weight of the polyalkylene oxide polymer is such that the compatible component remains compatible with the curing unsaturated polyester and monomer. When the molecular weight of the polymer is too high, the polyalkylene oxide polymer is incompatible with the curing unsaturated polyester and monomer. At that point the polyalkylene oxide polymer acts like a low-profile additive component, which, by definition, is incompatible with the curing unsaturated polyester and monomer. Specific examples of polyalkylene oxide polymers useful as compatible components include polyethylene oxide having a molecular weight between about 200–1000 and polyethylene oxide having a mole weight between about 200–5000.

Other examples of these compatible components include esters of citric acid, adipic acid and/or sebacic acid with tripropylene glycol monomethyl ether, dipropylene glycol monomethyl ether, diethylene glycol monomethyl ether, diethylene glycol monoethyl ether and the like.

Examples of esters include triesters of a general structure:

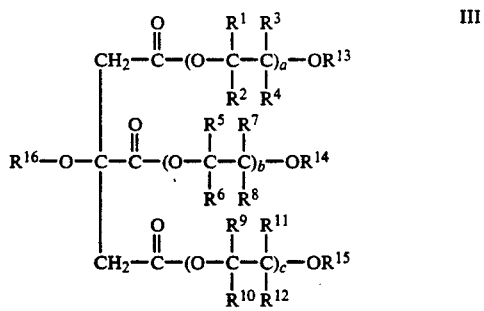

wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$ and $R^{16}$ are selected from the group consisting of hydrogen, cycloalkyl, lower alkyl, phenyl, phenyl substituted by halogen, lower alkyl, acyl, or lower alkoxy, and $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$ may be the same or different, a, b, and c are integers between 1 and about 200, and a, b and c may be the same or different.

Specific examples of such triesters include wherein $a=b\leq c=3$, $R^1=R^2=R^3=R^4=R^5=R^6=R^7=R^8=R^9=R^{10}=R^{11}=R^{12}=H$, $R^{13}=R^{14}=R^{15}=CH_3$, and $R^{16}=H$; and wherein $a=b=c=3$, $R^1$ or $R^2$ or $R^3$ or $R^4=CH_3$ and the others=H, $R^5$ or $R^6$ or $R^7$ or $R^8=CH_3$ and the others=H, $R^9$ or $R^{10}$ or $R^{11}$ or $R^{12}=CH_3$ and the others=H, $R^{13}=R^{14}=R^{15}=CH_3$ and $R^{16}=H$.

Still more examples of esters include diesters of a general structure:

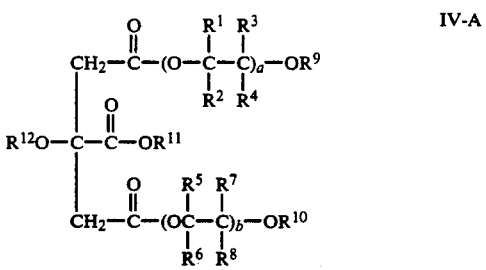

wherein $R^1$, $R^2$, $R^3$, $R^4$, $R^5$, $R^6$, $R^7$, $R^8$, $R^9$, $R^{10}$, $R^{11}$ and $R^{12}$ are selected from the group consisting of hydrogen, cycloalkyl, lower alkyl, phenyl, phenyl substituted by halogen, lower alkyl, acyl, or lower alkoxy, and $R^1$, $R^2$, $R^3$, $R^4$, $R^5$, $R^6$, $R^7$, $R^8$, $R^9$, $R^{10}$, $R^{11}$ and $R^{12}$ may be the same or different, a and b are integers between 1 and about 200 and b may be the same or different.

Specific examples of such diesters include wherein $a=b=3$, $R^1=R^2=R^3=R^4=R^5=R^6=R^7=R^8=H$, $R^9=R^{10}=CH_3$ and $R^{11}=R^{12}=H$; and wherein $a=b=3$, $R^1$ or $R^2$ or $R^3$ or $R^4=CH_3$ and the others=H, $R^5$ or $R^6$ or $R^7$ or $R^8=CH_3$ and the others=H, $R^9=R^{10}=CH_3$ and $R^4=R^{12}=H$.

Still more specific examples of esters include diesters of a general structure;

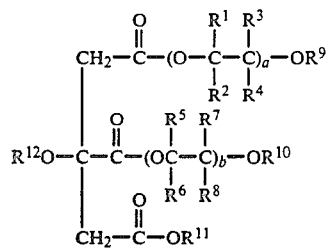

IV-B wherein $R^1$, $R^2$, $R^3$, $R^4$, $R^5$, $R^6$, $R^7$, $R^8$, $R^9$, $R^{10}$, $R^{11}$ and $R^{12}$ are selected from the group consisting of hydrogen, cycloalkyl, lower alkyl, phenyl, phenyl substituted by halogen, lower alkyl, acyl, or lower alkoxy, and $R^1$, $R^2$, $R^3$, $R^4$, $R^5$, $R^6$, $R^7$, $R^8$, $R^9$, $R^{10}$, $R^{11}$ and $R^{12}$ may be the same or different, a and b are integers between 1 and about 200 and b may be the same or different.

Specific examples of such diesters include wherein $a = b = 3$, $R^1 = R^2 = R^3 = R^4 = R^5 = R^6 = R^7 = R^8 = H$, $R^9 = R^{10} = CH_3$ and $R^{11} = R^{12} = H$; and wherein $a = b = 3$, $R^1$ or $R^2$ or $R^3$ or $R^4 = CH_3$ and the others = H, $R^5$ or $R^6$ or $R^7$ or $R^8 = CH_3$ and the others = H, $R^9 = R^{10} = CH_3$ and $R^{11} = R^{12} = H$.

Still more specific examples of esters include monoesters of a general structure:

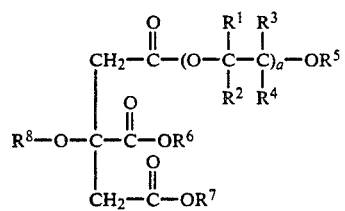

V-A $R^1$, $R^2$, $R^3$, $R^4$, $R^5$, $R^6$, $R^7$ and $R^8$ are selected from the group consisting of hydrogen, cycloalkyl, lower alkyl, phenyl phenyl substituted by halogen, lower alkyl, acyl, or lower alkoxy, and $R^1$, $R^2$, $R^3$, $R^4$, $R^5$, $R^6$, $R^7$ and $R^8$ may be the same or different, and a is an integer bewteen 1 and about 200.

Specific examples of such monoesters include wherein $a = 3$, $R^1 = R^2 = R^3 = R^4 = H$, $R^5 = CH_3$ and $R^6 = R^7 = R^8 = H$; and wherein $a = 3$, $R^1$ or $R^2$ or $R^3$ or $R^4 = CH_3$ and the others = H, $R^5 = CH_3$ and $R^6 = R^7 = R^8 = H$.

Still more specific examples of esters include monoesters of a general structure:

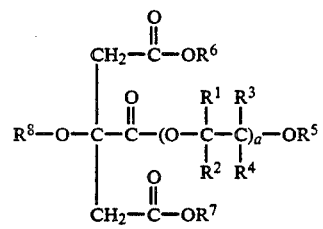

V-B $R^1$, $R^2$, $R^3$, $R^4$, $R^5$, $R^6$, $R^7$ and $R^8$ are selected from the group consisting of hydrogen, cycloalkyl, lower alkyl, phenyl, phenyl substituted by halogen, lower alkyl, acyl, or lower alkoxy, and $R^1$, $R^2$, $R^3$, $R^4$, $R^5$, $R^6$, $R^7$ and $R^8$ may be the same or different, and a is an integer between 1 and about 200.

Specific examples of such monoesters include wherein $a = 3$, $R^1 = R^2 = R^3 = R^4 = H$, $R^5 = CH_3$ and $R^6 = R^7 = R^8 = H$; and wherein $a = 3$, $R^1$ or $R^2$ or $R^3$ or $R^4 = CH_3$ and the others = H, $R^5 = CH_3$ and $R^6 = R^7 = R^8 = H$.

The invention also relates to a process for making citrate ester compounds of the general formula

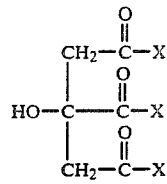

I wherein X is selected from the group consisting of -(-O-$C_3H_6$-)$_3$-OCH$_3$ and OH. The process comprises adding together approximately 25-30 percent, by weight, of citric acid and approximately 70-75 percent, by weight, of tripropylene glycol monomethyl ether, heating to a temperature in the range of about 190°-240° C. with a nitrogen sparge to remove water. The resulting product comprises approximately 5-50 and preferably about 32-42 percent, by weight of 2-hydroxy-1,2,3-propane tricarboxylic acid-tripropylene glycol monomethylether triester, approximately 5-95 and preferably about 46-57 percent, by weight, of 2-hydroxy-1,2,3-propane tricarboxylic acid-tripropylene glycol monomethylether diester, and approximately 5-50 and preferably about 5-5 percent, by weight, of 2-hydroxy-1,2,3-propane tricarboxylic acid-tripopylene glycol monomethylether monoester.

The citrate esters described in this invention may also be useful as plasticizers for thermoplastic polymers such as polyvinyl chloride, or polystyrene.

The four components resinous system is suitable for mixing with other ingredients in order to form a sheet molding composition. For example, the four component resinous system is suitable for mixing with chemical thickeners which are physically mixed into the resin emulsion. The chemical thickeners generally include metal oxides, hydroxides and aldoxides of Group II, III or IV from the Periodic Table. Calcium oxide and magnesium oxide or the respective hydroxides are most often employed with four component resin compositions of the present invention. In preferred embodiments, the thickener is present in amounts ranging from about 0.5 to about 6 parts, by weight, based on the four component resinous system. The thickener is generally suspended in a carrier resin, as is known in the art. In preferred embodiments the carrier material comprises a composition which does not react with the thickener such as, for example, polymethylmethacrylate, polyvinylacetate, saturated or unsaturated polyesters, and similar materials well-known in the art. In preferred embodiments the carrier resin is present in amounts ranging from about 0.5 to about 8 parts, by weight, based on one hundred parts of the four component resinous system.

Catalysts are incorporated in small amounts into thermosetting polyester resins containing ethylenically unsaturated monomer to aid in curing or crosslinking the unsaturated polyester with the monomer. Such catalysts are well known and may be similarly utilized in this invention to aid in curing the unsaturated polyester and monomer mixed with the low-profile thermoplastic polymer. Typical catalysts, for example, include organic peroxides and peracids such as tertiary butyl perbenzoate, tertiary butyl peroctoate, benzoyl peroxide and the like. The amounts of catalysts may be varied with the molding process and similarly varied with the level and types of inhibitors utilized, in a manner well known in the art. In preferred embodiments the catalyst is present in amounts ranging from about 0.5 to about 2.5 parts, by weight, based on one hundred parts of the four component resinous system.

Curing of the composition is carried out under heat and pressure typically, in closed, preferably positive pressure type molds. Mold release agents may be added to the compositions to perform their normal function, as is well understood in the art.

Fibers, fillers and pigments normally added to resin compositions can be likewise used in formulating the sheet molding composition of this invention. Reinforcing fibers or fibrous reinforcement is taken to mean glass fibers in one form or another, such as glass fabrics, chopped glass strands, chopped or continuous strand glass fiber mat; however, the terms also include reinforcing agents which may also be used if desired, for example asbestos, cotton, synthetic organic fibers and metals. Fillers, usually inert, and inorganic material useful with the compositions of the present invention include, for example, clay, talc, calcium carbonate, silica, calcium silicate, and the like. In preferred embodiments the fillers are present in amounts ranging from the 165 to about 250 parts, by weight, based on one hundred parts of the four component resinous system.

Examples of pigments include carbon black, iron oxide, titanium dioxide, and the like, as well as organic pigments. In preferred embodiments the pigments are present in amounts ranging from about 0 to about 4 parts, by weight, based on one hundred parts of the four components resinous system.

The preparation of the sheet molding composition is generally carried out by blending together a first portion comprising the unsaturated polyester, the low-profile additive, the monomer, the compatible component, and such additives as a catalyst, mold release agent and fillers. This is generally known in the industry as the A-side formulation. The second portion (generally known as the B-side formulation) comprises the thickening agent and a carrier resin therefor, and such additives as pigments and mold release agents. In another aspect of the invention an additional monomer is added to the B-side formulation in which the thickener is suspended. In preferred embodiments the additional monomer comprised vinyl toluene or styrene. In preferred embodiments, the additional monomer is present in amounts ranging from about 1 to about 8 parts, by weight, based on one hundred parts of the four component resinous system.

The sheet molding composition can be prepared by mixing the components in a suitable apparatus at temperatures which are conventional and known to those skilled in the art. Once the sheet molding composition is formulated, the composition can be molded into thermoset articles having a desired shape. The actual molding cycle will, or course, depend upon the exact composition being molded. In preferred embodiments suitable molding cycles are conducted at temperatures ranging from about 250°-350° F. for periods of time ranging from about ½ to about 5 minutes.

The following formulations are provided to illustrate examples of the compositions of the present invention and are not intended to restrict the scope thereof. All parts are parts by weight, unless otherwise expressly specified.

TABLE I

Resin Compositions

| Ingredients | Range (wt. %) | Preferred Range (wt. %) |
|---|---|---|
| Unsaturated polyester | 20–45 | 28–35 |
| Thermoplastic additive (low-profile) | 5–30 | 7–20 |
| Monomer | 25–65 | 35–50 |
| Compatible component | 0.5–15 | 1–8 |
| | 100 | 100 |

TABLE II

Typical Sheet Molding Composition Formulation

| Ingredients | Formulations | | | |
| | A | B | C | D |
|---|---|---|---|---|
| Resin | 100 | 100 | 100 | 100 |
| Catalyst | 1.5 | 1.5 | 1.5 | 1.5 |
| Release agent | 5.0 | 4.5 | 5.0 | 4.5 |
| Filler | 230 | 220 | 225 | 225 |
| Thickener | 4.0 | 5.0 | 4.5 | 4.8 |
| Pigment | 0.1 | 0.2 | 0.1 | 0.1 |
| Carrier | 1.55 | — | 1.5 | 1.6 |
| Secondary monomer | 5.6 | — | 5.5 | 5.5 |

The sheet molding compositions of the above formulations have shown unexpected improvements in surface aesthetics and mold fillout. These improvements are especially significant for use in sheet molding compounds (SMC). Moreover, increasingly thinner automobile parts are able to be molded with smoother surfaces than by any known systems.

For formulation A the unsaturated polyester comprises maleic anhydride and propylene giycol; the low-profile additive comprises a saturated polyester made from ethylene glycol and propylene glycol and adipic acid; the monomer comprises styrene; the compatible component comprises a polypropylene oxide having a molecule weight between about 200 and 2000; the catalyst comprises tertiary butyl perbenzoate; added to the A-side, the release agent comprises calcium stearate and zinc stearate; the filler comprises calcium carbonate; the thickener comprises magnesium hydroxide; the carrier comprises polymethylmethacrylate; the pigment comprises a carbon black pigment suspension; and the secondary monomer comprises vinyl toluene.

Compression molded panels were made with each formulation with 27 percent, by weight, of 1" chopped glass fibers. When measured on a surface smoothness index instrument (LORIA ® registered trademark of the Ashland Chemical Co.) the panels gave the LORIA ® number of 60–70 as compared to the same formulation but without any compatible component which gave a number of 80–90. On the LORIA ® instrument, the lower the number, the smoother the surface.

For formulation B the unsaturated polyester comprises maleic anhydride and propylene glycol; the low-profile additive comprises a saturated polyester made from ethylene glycol and propylene glycol and adipic acid; the monomer comprises styrene; the compatible component comprises a triester of citric acid with tripropylene glycol monomethyl ether; the catalyst comprises tertiary butyl perbenzoate; the release agent comprises calcium stearate; the filler comprises calcium carbonate; the thickener comprises magnesium hydroxide; and the pigment comprises a carbon black pigment suspension.

Compression molded panels made with Formulation B with 27 percent, by weight, of 1" chopped glass fibers. When measured on a surface smoothness index instrument (LORIA ®) the panels gave a number of 55-60 as compared to the same formulation but without he compatible component which gave a number 80-90.

For formulation C the unsaturated polyester comprises maleic anhydride and propylene glycol; the low-profile additive comprises a saturated polyester made from ethylene glycol and propylene glycol and adipic acid; the monomer comprises styrene; the compatible component comprises polypropylene oxide having a molecular weight of approximately 700 and citrate esters of the general formulae III, IV-A and IV-B, and V-A and V-B, wherein the polypropylene oxide comprises approximately 3 percent and the citrate esters comprise approximately 4 percent, by weight, of the resin formulation; the catalyst comprises tertiary butyl perbenzoate; the release agent comprises zinc stearate; the filler comprises calcium carbonate; the thickener comprises magnesium hydroxide; the carrier comprises polymethylmethacrylate; the pigment comprises a carbon black pigment suspension; and the secondary monomer comprises vinyl toluene.

Compression molded panels were made with formulation C with 27 percent, by weight, 1" chopped glass fibers. When measured on a surface smoothness index instrument, LORIA ®, the panels gave a number of 50 as compared to the same formulation without he compatible component which gave a number of 80-90.

For formulation D the unsaturated polyester comprises maleic anhydride and propylene glycol; the low profile additive comprises a saturated polyester made from ethylene glycol and propyleneglycol and adipic acid; the monomer comprises styrene; the compatible component comprises polypropylene oxide having a molecular weight of approximately 700 and citrate esters of the general formulae III, IV-A, IV-B and V-A and V-B wherein the polypropylene oxide comprises approximately 3 percent and the citrate esters comprise approximately 4 percent, by weight, of the resin formulation; the catalyst comprises tertiary butyl perbenzoate; the release agent comprises calcium stearate; the filler comprises calcium carbonate; the thickener comprises 4 parts per hundred resin magnesium hydroxide and 0.8 parts per hundred magnesium oxide; the carrier comprises polyvinylacetate; the pigment comprises a carbon black pigment suspension; and the secondary monomer comprises vinyl toluene.

Compression molded panels were made with formulation D with 27 percent, by weight, of 1" chopped glass fibers. When measured on a surface smoothness index instrument, LORIA ®, the panels gave an umber of 48 as compared to the same formulation without he compatible components which gave a number of 80-90.

Although the invention has been described in its preferred form with a certain degree of particularity, it is understood that the present disclosure has been made only by way of example, and that numerous changes can be made without departing from the spirit of the scope of the invention.

We claim:

1. An ester compound of the formula

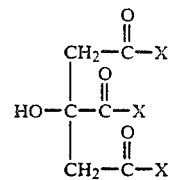

formed by the process of claim 16 wherein X is selected from the group consisting of (O—$C_3H_6$)$_3$—$OCH_3$ and OH.

2. The compound of claim 1, wherein the ester is a 2-hydroxy-1,2,3-propane tricarboxylic acid-tripropylene glycol monomethylether triester having a general structure:

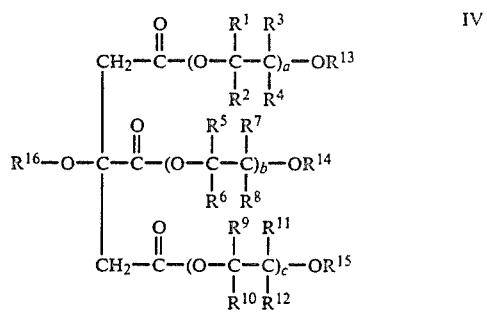

wherein a=b=c=3, $R^1$ or $R^2$ or $R^3$ or $R^4$=$CH_3$ and the others=H, $R^5$ or $R^6$ or $R^7$ or $R^8$=$CH_3$ and the others=H, $R^9$ or $R^{10}$ or $R^{11}$ or $R^{12}$=$CH_3$ and the others=H, $R^{13}$=$R^{14}$=$R^{15}$=$CH_3$ and $R^{16}$=H.

3. The compound of claim 1, wherein the ester is a 2-hydroxy-1,2,3-propane tricarboxylic acid-tripropylene glycold monomethyl ether diester having a general structure:

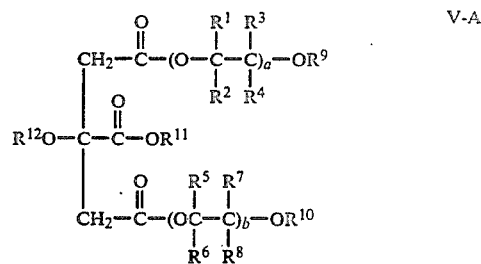

wherein a=b=3, $R^1$ or $R^2$ or $R^3$ or $R^4$=$CH_3$ and the others=H, $R^5$ or Rhu 6 or $R^7$ or $R^8$=$CH_3$ and the others=H, $R^9$=$R^{10}$=$R^{11}$=$CH_3$ and $R^{12}$=H.

4. The compound of claim 1, wherein the ester is a 2-hydroxy-1,2,3-propane-tricarboxylic acid-tripropylene glycol monomethyl ether diester having a general structure:

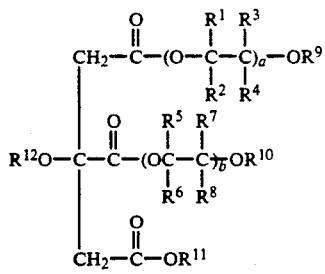

V-B wherein a=b=3, $R^1$ or $R^2$ or $R^3$ or $R^4$=CH$_3$ and the others=H, $R^5$ or $R^6$ or $R^7$ or $R^8$=CH$_3$ and the others=H, $R^9$=$R^{10}$=$R^{11}$=CH$_3$ and $R^{12}$=H.

5. The compound of claim 1, wherein the ester is a 2-hydroxy-1,2,3-propane carboxylic acid-tripropylene glycol monoethylether monoester having a general structure:

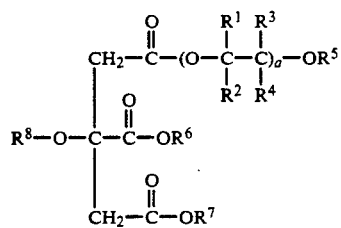

VI-A wherein $R^1$ or $R^2$ or $R^3$ or $R^4$=CH$_3$ and others=H, $R^5$=$R^6$=$R^7$=CH$_3$ and $R^8$=H.

6. The compound of claim 1, wherein the ester is a 2-hydroxy-1,2,3-propane-tricarboxylic acid-tripropylene glycol monomethylether monester having a general structure:

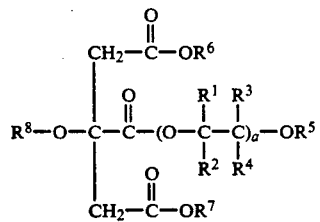

VI-B wherein $R^1$ or $R^2$ or $R^3$ or $R^4$=CH$_3$ and the others=H, $R^5$=$R^6$=$R^7$=CH$_3$ and $R^8$=H.

7. A four component resinous system for a sheet molding composition comprising:
  (a) an unsaturated polyester comprising a polycondensation product of one or more dihydric alcohols and one or more ethylenically unsaturated polycarboxylic acids;
  (b) one or more low-profile thermoplastic polymers which cause phase separation and internal voids during a curring reaction;
  (c) one or more olefinically unsaturated monomers which copolymerizes with the unsaturated polyester; and
  (d) one or more compatible components comprising one or more ester compounds of the formula

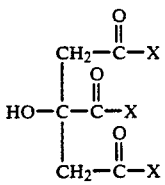

wherein X is selected from the group consisting of (O—C$_3$H$_6$)$_3$—OCH$_3$ and OH.

8. The resinous system of claim 7, wherein the compatible components comprise a mixture of 2-hydroxy-1,2,3-propane tricarboxylic acid-tripropylene glycol monomethylether triester, diesters and monoesters.

9. The composition of claim 7, wherein the unsaturated polyester comprises the polycondensation product of dihydric alcohols and an ethylenically unsaturated polycarboxylic acid.

10. The composition of claim 7, wherein the unsaturated polyester comprises the polycondensation product of maleic and/or fumaric acids and propylene glycol; the polycondensation product of 1,3-butanediol and maleic and/or fumaric acids; the polycondensation product of ethylene and propylene glycols comprising approximately 50 mole percent or less of ethylene glycol, and maleic and/or fumaric acids; the polycondensation product of propylene glycol, maleic and/or fumaric acids and dicyclopentadiene reacted with water; or, the polycondensation product of propylene glycol, maleic and/or fumaric acids and isophtalic acid.

11. The composition of claim 7, wherein the low-profile thermoplastic polymer comprises a reaction product of ethylene glycol and propylene glycol and adipic acid; a polyvinyl acetate homopolymer or copolymer; or, a polymethylmethacrylate.

12. The composition of claim 7, wherein the monomer comprises styrene; methyl-styrene; or, vinyl toluene.

13. The composition of claim 7, wherein the unsaturated polyester is present in an amount of approximately 25-45 percent, by weight, of the four component resin; the low-profile thermoplastic polymer is present in an amount of approximately 5-30 percent, by weight, of the four component resin; the monomer is present in an amount of approximately 25-65 percent, by weight, of the four component resin; and the compatible component is present in an amount of approximately 0.5-15 percent, by weight, of the four component resin.

14. The composition of claim 7, wherein the unsaturated polyester is present in an amount of approximately 28-35 percent, by weight, of the four component resin; the low-profile thermoplastic polymer is present in an amount of approximately 7-15 percent, by weight, of the four component resin; wherein the monomer is present in an amount of approximately 35-65 percent, by weight, of the four component resin; the compatible component is present in an amount of approximately 1-8 percent, by weight, of the four component resin.

15. The composition of claim 14, wherein the compatible component comprises polypropylene oxide having a molecular weight of about 700 and a mixtue of 2-hydroxy-1,2,3-propane tricarboxylic acid-tripropylene glycol monomethylether triester, diesters and monoesters.

16. A process for making citrate esters compounds of the general formula

15

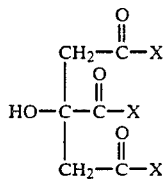

wherein X is selected form the group consisting of (OC₃H₆)OCH₃ and OH, comprising adding together approximately 25–30 percent, by weight, of citric acid and approximately 70–75 percent, by weight, of tripropylene glycol monomethyl ether and heating to a temperature in the range of about 190°–240° C.

* * * * *

16

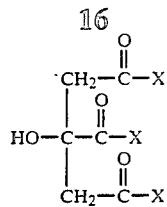

wherein X is selected form the group consisting of —OC₃H₆)OCH₃ and OH, comprising adding together approximately 25–30 percent, by weight, of citric acid and approximately 70–75 percent, by weight, of tripropylene glycol monomethyl ether and heating to a temperature in the range of about 190°–240° C.

* * * * *